United States Patent [19]
Yan

[11] Patent Number: 5,846,503
[45] Date of Patent: Dec. 8, 1998

[54] PROCESS FOR REJUVENATING USED ALKANOLAMAINE SOLUTIONS

[75] Inventor: Tsoung Y. Yan, Philadelphia, Pa.

[73] Assignee: Mobil Oil Corporation, Fairfax, Va.

[21] Appl. No.: 887,404

[22] Filed: May 19, 1992

Related U.S. Application Data

[63] Continuation of Ser. No. 628,311, Dec. 17, 1990, abandoned.

[51] Int. Cl.$^6$ .......................... C07C 209/84; B01D 53/52
[52] U.S. Cl. .......................... 423/228; 423/229; 423/246; 210/757; 564/497
[58] Field of Search .................................. 423/228, 229, 423/226, 246; 210/766, 757; 564/497, 487, 488, 489

[56] References Cited

U.S. PATENT DOCUMENTS

| | | | |
|---|---|---|---|
| 2,768,945 | 10/1956 | Shapiro | 423/229 |
| 3,207,790 | 9/1965 | Glew et al. | 564/467 |
| 3,429,804 | 2/1969 | Sze et al. | 585/271 |
| 3,546,103 | 12/1970 | Hamner et al. | 208/211 |
| 3,598,881 | 8/1971 | Kniel et al. | 585/613 |
| 3,696,162 | 10/1972 | Kniel | 55/73 |
| 3,755,145 | 8/1973 | Orkin | 208/111 |
| 3,894,938 | 7/1975 | Gorring et al. | 208/97 |
| 3,911,082 | 10/1975 | Rottmayr et al. | 423/226 |
| 3,926,591 | 12/1975 | Wildmoser et al. | 423/229 |
| 4,113,837 | 9/1978 | Kendall et al. | 423/226 |
| 4,225,421 | 9/1980 | Hensley, Jr. et al. | 208/216 |
| 4,343,777 | 8/1982 | Dannhorn et al. | 423/229 |
| 4,411,770 | 10/1983 | Chen et al. | 208/111 |
| 4,440,630 | 4/1984 | Oleck et al. | 208/111 |
| 4,456,700 | 6/1984 | Oleck et al. | 502/220 |
| 4,458,024 | 7/1984 | Oleck et al. | 502/66 |
| 4,548,709 | 10/1985 | Bowes et al. | 208/213 |
| 4,600,503 | 7/1986 | Angevine et al. | 208/251 H |
| 4,696,732 | 9/1987 | Angevine et al. | 208/111 |
| 4,795,565 | 1/1989 | Yan | 210/669 |
| 4,937,834 | 6/1990 | Dobson | 564/488 |
| 4,954,325 | 9/1990 | Rubin et al. | 502/64 |
| 5,152,887 | 10/1992 | Beasley | 423/229 |

OTHER PUBLICATIONS

K.F. Butwell, D.J. Kubec and P.W. Sigmund, "Alkanolamine Treating", Hydrocarbon Processing, Mar., 1982.
Martin, J.F. "Reduce Olefin Plant Fouling", in Hydrocarbon Processing, Nov., 1988, pp. 63–67.

*Primary Examiner*—Michael L. Lewis
*Assistant Examiner*—Peter DiMauro
*Attorney, Agent, or Firm*—Robert B. Furr, Jr.; Malcolm D. Keen

[57] ABSTRACT

The present invention provides a method for rejuvenating an aqueous alkanolamine solution being at least partially deactivated from contact with an acid gas, said rejuvenation method comprising contacting said aqueous alkanolamine solution with hydrogen in the presence of a hydrotreating catalyst under hydrotreating conversion conditions including contact time sufficient to increase the acid gas sorption capacity of said aqueous alkanolamine solution.

30 Claims, 1 Drawing Sheet

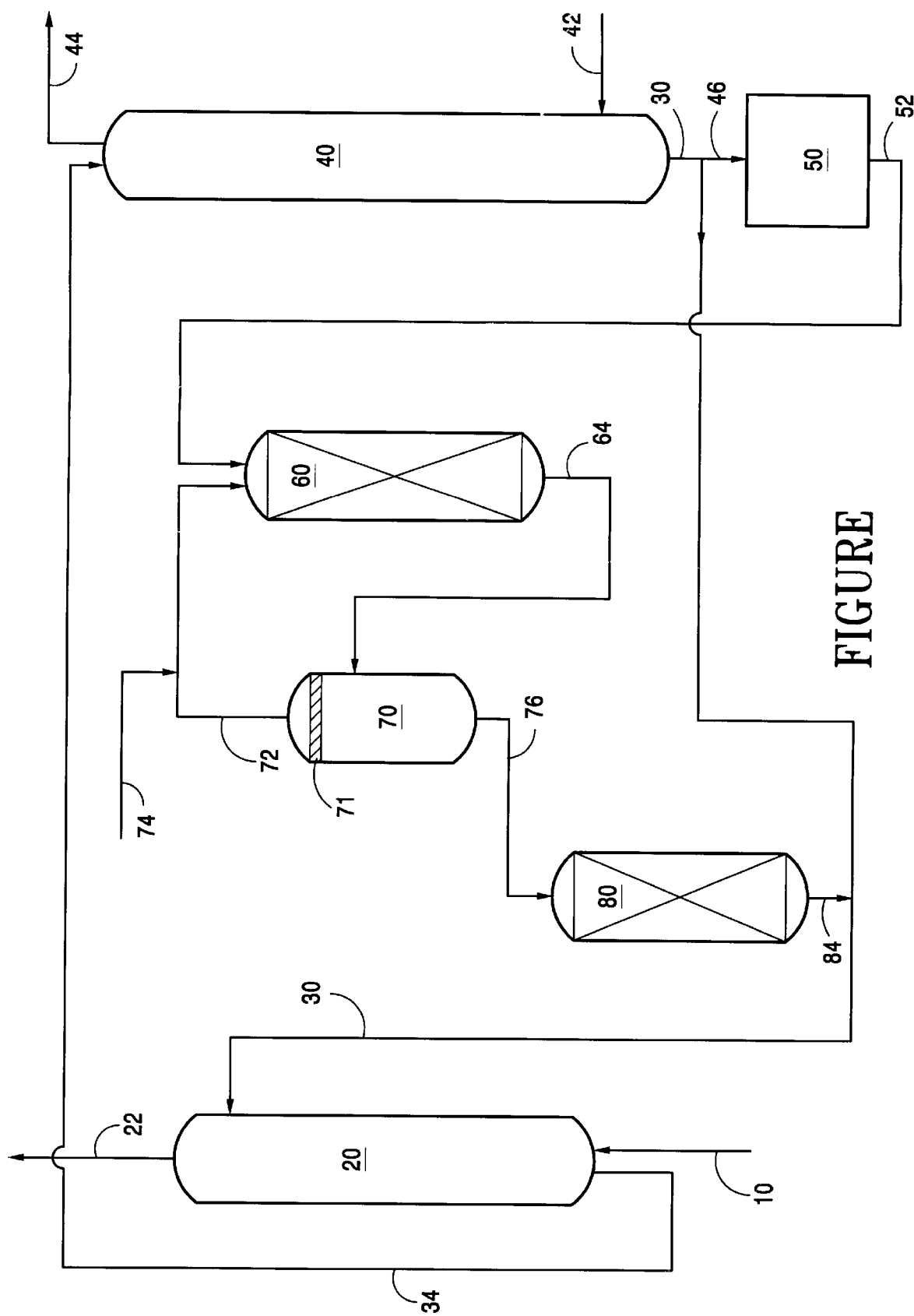
FIGURE

PROCESS FOR REJUVENATING USED ALKANOLAMAINE SOLUTIONS

This is a continuation of application Ser. No. 07/628,311 filed on Dec. 17, 1990, now abandoned.

FIELD OF THE INVENTION

The present invention relates to the rejuvenation of alkanolamine solutions useful to sorb acid gas constituents from a gas stream. More specifically, the invention relates to a method for hydrotreating used alkanolamine solutions to reduce corrosivity and to restore acid gas sorption capacity.

BACKGROUND OF THE INVENTION

Alkanolamine process units remove $H_2S$ and $CO_2$ from gaseous process streams, typically by countercurrently contacting an aqueous solution containing from about 20% to about 50% by weight of an alkanolamine with a gas stream containing $H_2S$ and/or $CO_2$. For the purpose of this disclosure, it is understood that the terms "alkanolamine" and "ethanolamine" are generic terms including, but not limited to, monoethanolamine, diethanolamine, triethanolamine, and methyl diethanolamine.

The removal of hydrogen sulfide from gaseous streams, such as the waste gases liberated in the course of various chemical and industrial processes, for example, in wood pulping, natural gas and crude oil production and in petroleum refining, has become increasingly important in combating atmospheric pollution. Hydrogen sulfide containing gases not only have an offensive odor, but such gases may cause damage to vegetation, painted surfaces and wildlife, and further may constitute a significant health hazard to humans. Government-wide regulations have increasingly imposed lower tolerances on the content of hydrogen sulfide which can be vented to the atmosphere, and it is now imperative in many localities to remove virtually all the hydrogen sulfide under the penalty of an absolute ban on continuing operation of a plant or the like which produces the hydrogen sulfide-containing gaseous stream. Solutions of water and one or more the alkanolamines are widely used in industry to remove hydrogen sulfide and carbon dioxide from such gaseous streams.

Corrosion in alkanolamine units significantly increases both operating and maintenance costs, and more importantly, may pose a safety risk because the rate of corrosive attack can precipitously and unexpectedly accelerate in response to changing process conditions. The mechanisms of corrosive attack include general corrosive thinning, pitting, corrosion-erosion, and stress-corrosion cracking. Corrosion control techniques include the use of more expensive corrosion and erosion resistant alloys, continuous or periodic removal of corrosion-promoting agents by filtration or by activated carbon adsorption, or by the addition of corrosion inhibitors. (See Kohl, A. L. and Reisenfeld, F. C., *Gas Purification*, Gulf Publishing Company, Houston, 1979, pp. 91–105, as well as K. F. Butwell, D. J. Kubec and P. W. Sigmund, "Alkanolamine Treating", *Hydrocarbon Processing*, March, 1982.)

Further, it has been found that the acid gas sorption capacity in a circulating alkanolamine-water system decreases with time on stream which necessitates constant or periodic addition of makeup alkanolamine. This performance degradation has been found to be partially attributable to the accumulation of heat stable salts including acid salts of alkanolamines. U.S. Pat. No. 4,795,565 to Yan describes a process for removing heat stable salts from an ethanolamine system by the use of ion exchange resins. The disclosure of U.S. Pat. No. 4,795,565 to Yan is incorporated herein by reference for the operating details both of an ethanolamine acid gas sorption system as well as for the heat stable salt removal process.

Heat stable salts may also be removed from an alkanolamine system by distillation. However, such separation has been limited in the past to relatively mild conditions of temperature and pressure to avoid thermal degradation of the alkanolamine. For example, diethanolamine (DEA) boils at 268° C. at 760 mm Hg pressure and tends to oxidize and decompose at high temperature. For this reason, vacuum distillation has not been widely used to separate heat stable salts from spent alkanolamine solutions.

Further, it has been found that degradation products formed during the alkanolamine/acid gas sorption cycle accumulate in the circulating alkanolamine solution and decrease its acid gas sorption capacity. Removing these degradation products from the alkanolamine solution would improve the acid gas sorption capacity of the remaining solution, but such removal has been found to have limited practical utility for several reasons. First, the degradation products boil at ranges of temperatures near the parent alkanolamine, thus complicating distillation. Second, even if the degradation products could readily be fractionated from the parent alkanolamine, the rejected degradation products would require special handling and disposal as hazardous wastes.

To reiterate, prior to the advent of the present invention, a stream enriched in alkanolamine degradation products would be considered a waste stream, and would require handling as a hazardous waste stream due to its toxicity and corrosivity. If, however, the alkanolamine degradation products accumulated in the used alkanolamine solution could be readily converted to a useful product, these degradation products would no longer comprise a waste stream, but would be a valuable intermediate product stream. More specifically, if the alkanolamine degradation products generated in alkanolamine acid gas sorption could be readily converted to compounds useful for acid gas sorption, the alkanolamine acid gas sorption process could be operated continuously, with minimal alkanolamine makeup requirements while generating essentially no organic hazardous waste.

The chemistry of alkanolamine degradation is discussed in the Butwell et al. article cited above. Briefly, the Butwell et al. article notes that monoethanolamine (MEA) irreversibly degrades to N-(2-hydroxyethyl) ethylene diamine (HEED). HEED shows reduced acid gas removal properties and becomes corrosive at concentrations of at least about 0.4% by weight.

Diglycolamine (DGA), on the other hand, is said to produce a degradation product upon reaction with $CO_2$ which exhibits different properties. DGA, a registered trademark of Texaco, Inc., identifies an amine having the chemical formula $NH_2—C_2H_4—O—C_2H_4—OH$. DGA degrades in the presence of $CO_2$ to form N,N'-bis (hydroxyethoxyethyl) urea (BHEEU) which is similar to HEED in corrosivity but differs in that BHEEU has no acid gas removal properties.

Diethanolamine (DEA) reacts with $CO_2$ to form N,N'-di (2-hydroxyethyl) piperazine. Unlike HEED and BHEEU, the piperazine compound is noncorrosive and has acid gas removal properties essentially equal to its parent, DEA. See the Butwell et al. article at page 113.

Diisopropylamine (DIPA) readily degrades in the contact with $CO_2$ to form 3-(2-hydroxypropyl) 5-methyl oxazolidone which shows essentially no acid gas removal properties. See the Butwell et al. article at page 113.

Numerous degradation products formed by the reaction of $H_2S$, or a mixture of $H_2S$ and $CO_2$ with diethanolamine have been reported from analyses of operating diethanolamine acid gas sorption processes and are shown below in Table 1.

See in this regard U.S. Pat. No. 4,080,296. U.S. Pat. No. 3,546,103. teaches hydrodesulfurization with a catalyst which includes cobalt and molybdenum on an alumina base. U.S. Pat. No. 3,755,145 describes a process for preparing lube oils, characterized by low pour points, which utilizes a catalyst mixture comprising hydrogenation components, a

TABLE 1

COMPOUNDS RESULTING FROM DEA DEGRADATION

| Name | Abbreviation | Structural formula |
|---|---|---|
| N,N-Bis (2-hydroxyethyl) piperazine | HEP | $HO-CH_2-CH_2-N(CH_2-CH_2)_2N-CH_2-CH_2-OH$ |
| N,N,N-tris (2-hydroxyethyl) ethylenediamine | THEED | $(HO-CH_2-CH_2)_2N-CH_2-CH_2-NH-CH_2-CH_2-OH$ |
| Hydroxyethyl imidazolidone | HEI | cyclic: $CH_2-CH_2-N(CH_2CH_2OH)-C(=O)-NH-CH_2$ |
| N-Methyldiethanolamine | MDEA | $(HO-CH_2-CH_2)_2N-CH_3$ |
| Oxazolidone | OZO | cyclic: $CH_2-NH-C(=O)-O-CH_2$ |
| Aminoethylethanolamine | AEEA | $NH_2-CH_2-CH_2-NH-CH_2-CH_2-OH$ |
| Bis-(2-hydroxy ethyl) glycine | BHG | $(HO-CH_2-CH_2)_2N-CH_2-C(=O)-OH$ |

Commonly assigned U.S. application Ser. No. 525,582, filed May 21, 1990, to Yan teaches a method for restoring the acid sorption capacity of an alkanolamine solution by holding the solution at elevated temperature for a period of time sufficient to convert the alkanolamine degradation products into alkanolamine derivatives which exhibit higher acid gas sorption capacity and lower corrosivity than their alkanolamine degradation product precursors.

Hydrotreating is a well known method for removing sulfur and nitrogen compounds from hydrocarbon stocks, and is carried out at elevated temperature and pressure in the presence of a hydrogenation catalyst. Hydrogenation components include Group IVA or Group VIII metals, or their oxides or sulfides. While the following references show that hydrotreating of petroleum stocks is a widely used upgrading technique, the hydrotreating process has not been applied to restore the acid gas sorption capacity and to reduce the corrosivity of spent alkanolamine streams.

Support materials for use with hydrotreating catalysts include a broad range of carriers including alumina, silica, silica-alumina, clay, kieselguhr, zeolitic molecular sieves, active carbon and other materials having high surface areas.

conventional cracking catalyst which can be either crystalline or amorphous and a crystalline aluminosilicate zeolite having a Constraint Index of 1 to 12.

U.S. Pat. No. 3,894,938 relates to the catalytic dewaxing and desulfurization of high pour point, high sulfur gas oils to lower their sulfur content by contacting such a gas oil with a hydrodewaxing catalyst having a Constraint Index of from 1 to 12, for example a catalyst comprising a zeolite having the structure of ZSM-5, which may contain a hydrogenation/dehydrogenation component, by conventional hydrodesulfurization processing of the dewaxed intermediate.

U.S. Pat. No. 4,440,630 relates to a single stage catalyst system and process for using the system in a single stage operation for hydrodewaxing and hydrotreating petroleum residua. The catalyst comprises a zeolite having the structure of ZSM-5 in an alumina binder having specified metal content and pore volume characteristics.

U.S. Pat. Nos. 4,456,700 and 4,458,024 relate to a process for hydrodewaxing and hydrotreating petroleum residua to more valuable products. The catalyst system described in the '024 patent includes a zeolite having a Constraint Index of 1 to 12, an alumina binder, at least one Group VIII metal selected from nickel, cobalt, and iron, and at least one Group VIB metal.

U.S. Pat. No. 4,225,421 describes a process for hydrodemetallation and hydrodesulfurization of a hydrocarbon feedstock containing asphaltenes and metals by contacting the feedstock with hydrogen and a bimodal catalyst which contains at least one metal, e.g., molybdenum, chromium, and tungsten.

U.S. Pat. No. 4,411,770 describes a process for the hydroconversion of heavy hydrocarbon oils, wherein the catalyst comprises a crystalline zeolite component and a metallic hydrogenation component. The zeolites taught as being useful in this process include zeolites having a Constraint Index of from 1 to 12 and zeolite Beta.

The article, T. Y. Yan, "Zeolite Based Catalyst for Hydrocracking", 22 *Ind. Eng. Chem. Process Des. Dev.* 154–160 (1983), relates to a zeolite/amorphous dual catalyst system developed for hydrocracked feeds with wide boiling range.

U.S. Pat. No. 4,696,732 discloses a process for simultaneously hydrotreating and dewaxing petroleum fractions. The process utilizes a single catalyst system which includes a hydrotreating component impregnated on a controlled pore size base and at least two catalyst components selected from any of an intermediate pore zeolite, a large pore zeolite, a zeolite Beta, and a large pore non-zeolite catalyst.

U.S. Pat. No. 4,600,503 teaches a method for hydrotreating residual oil which comprises utilizing a hydrotreating catalyst which contains a thermally stable composition comprising a layered metal oxide.

U.S. Pat. No. 4,548,709 describes the demetallation and desulfurization of residual oils by adding the oil to an aromatic solvent and contacting the mixture in the presence of hydrogen with an alumina having dual pore size distribution in the ranges of 90 to 200 Angstrom units and 1000 to 5000 Angstrom units.

U.S. Pat. No. 4,518,485 teaches a process for dewaxing a hydrocarbon feedstock with a relatively high pour point containing paraffin selected from a group of normal paraffins and slightly branched paraffins and sulfur and nitrogen compounds which comprises hydrotreating oil under conversion conditions sufficient to remove at least a portion of the sulfur and nitrogen compound and subjecting the hydrotreated oil to catalytic dewaxing by contacting the oil with a catalyst comprising zeolite Beta having a silica/alumina ratio of at least 30:1 and a hydrogenation/dehydrogenation component under isomerization conditions.

Prior to the advent of the present invention, however, catalytically hydrotreating alkanolamine solutions to restore their acid gas sorption capacity has not been considered.

SUMMARY OF THE INVENTION

The present invention provides a method for restoring the acid gas sorption capacity and reducing the corrosivity of the alkanolamine solution. Surprisingly, is has been found that an alkanolamine solution which has been deactivated by contact with acid gas can be effectively rejuvenated by contact with hydrogen in the presence of a hydrotreating catalyst under elevated temperature conditions.

The present invention provides, in a first aspect, a method for rejuvenating an aqueous alkanolamine solution being at least partially deactivated from contact with an acid gas, said rejuvenation method comprising contacting said aqueous alkanolamine solution with hydrogen in the presence of a hydrotreating catalyst under hydrotreating conversion conditions including contact time sufficient to increase the acid gas sorption capacity of said aqueous alkanolamine solution.

In a second aspect, the invention comprises a process for rejuvenating a used aqueous alkanolamine solution to restore its acid gas sorption capacity comprising the steps of:

(a) providing a used aqueous alkanolamine solution containing diethanolamine and a degradation product of said diethanolamine, said degradation product produced by the reaction of $H_2S$, $CO_2$ or CO and diethanolamine, said degradation product having a lesser affinity for dissolving $H_2S$, $CO_2$ or CO than its diethanolamine precursor;

(b) heating said aqueous mixture of step (a) to elevated temperature and holding said aqueous solution of step (a) at said elevated temperature in the presence of a hydrotreating catalyst under hydrogen partial pressure for a period of time sufficient to convert at least a portion of said diethanolamine degradation product to restore the acid gas sorption capacity of said used aqueous alkanolamine solution.

In a third aspect, the invention comprises a process for removing at least one selected from the group consisting of $H_2S$, $CO_2$ and CO from a hydrocarbon gas stream containing the same comprising the steps of:

(a) providing a hydrocarbon gas stream containing a recoverable concentration of at least one selected from the group consisting of $H_2S$, $CO_2$ and CO;

(b) contacting said hydrocarbon gas stream of step (a) with an aqueous alkanolamine solution containing alkanolamine to remove at least one of $H_2S$, $CO_2$ and CO from said hydrocarbon gas stream, and to convert at least a portion of said alkanolamine to degradation products having a lesser affinity for sorbing acid gases than said alkanolamine, and to evolve an alkanolamine solution enriched in at least one selected from the group consisting of $H_2S$, $CO_2$ and CO;

(c) stripping at least one of $H_2S$, $CO_2$ or CO from said enriched alkanolamine solution of step (b) to evolve a lean alkanolamine solution containing both alkanolamine and said alkanolamine degradation products;

(d) heating at least a portion of said lean aqueous alkanolamine stream of step (c) to elevated temperature and holding said lean aqueous alkanolamine solution of step (c) at said elevated temperature under hydrogen partial pressure in the presence of a hydrotreating catalyst for a period of time sufficient to convert at least a portion of said alkanolamine degradation product to restore the acid gas sorption capacity of said lean aqueous alkanolamine solution.

The process may further include an ion exchange step to remove inorganic heat stable salts, for example, as taught in U.S. Pat. No. 4,795,565 to Yan.

DESCRIPTION OF THE DRAWINGS

The Figure is a simplified block diagram showing the major processing steps of the present invention.

DETAILED DESCRIPTION

The alkanolamine solution regeneration procedure of the present invention may be conducted in a batch or continuous mode. The continuous mode is preferred, and it is still more preferred to continuously regenerate a slipstream of lean alkanolamine solution comprising from about 1 to about 50% of the total alkanolamine stream by weight, preferably from about 2 to about 30% of the total alkanolamine stream by weight, more preferably from about 4 to about 20% of the total alkanolamine stream by weight. The relative flow of the slipstream depends on the extent of alkanolamine degradation in the acid gas sorption system as well as the allowable level of alkanolamine degradation products in the system.

Alkanolamines

The alkanolamine regeneration process of the present invention restores acid gas sorption capacity to an aqueous alkanolamine solution containing degradation products, examples of which are shown in Table 1.

Suitable alkanolamines include, for example, monoethanalamine, diethanolamine, triethanolamine, monoisopropanolamine, diisopropanolamine, and triisopropanolamine, merely to name a few. For further background on the chemistry of alkanolamines, see 1 Kirk-Othmer Encyclopedia of Chemical Technology, 944 (1978). Particularly preferred alkanolamines include monoethanolamine, diethanolamine, triethanolamine and methyl diethanolamine.

Catalysts

The regeneration process of the present invention proceeds under hydrogen pressure in the presence of a hydrotreating catalyst of the type typically used in the petroleum refining industry for desulfurization, denitrogenation, and demetallation of hydrocarbonaceous feedstocks. Suitable catalysts include metals on an inert or catalytically active support as a heterogeneous catalyst. Useful heterogeneous catalysts may contain metals from Groups IB, IVB or VIIIA of the Periodic Table of the Elements, published by Sargent-Welch of Skokie, Ill. (catalog no. S-18806). Sulfides and oxides of these metals are also useful catalyst components. Specific examples of useful metals, metallic oxides and sulfides within these groups are exemplified by sulfides and oxides of Ni, Mo, W, Co, Pt, Pd, W, Cu, and Cr. Bimetallic catalysts including Ni-Mo, Ni-W, Co-Mo, Mo, Ni, Pt, Pd, W, and Cu-Cr are particularly preferred.

Both inert and catalytically active supports may be employed, with examples including one or more of alumina, silica, silica-alumina, zeolites, clays, Kieselguhr, titania, magnesia and active carbons from sources such as coal, coke, and coconut shell. Inert supports such as alumina, silica, and silica-alumina are particularly preferred.

The above-listed metals may also be exchanged onto zeolites to provide a zeolite catalyst having dehydrogenation activity. Metals may also be added to the zeolite by impregnation, mulling, mixing, coprecipitation, or a combination of one or more of these techniques. While zeolites are effective for use in the present rejuvenation process, their use may limit process flexibility. Specifically, zeolites are suitable for extended continuous process operation if the aqueous alkanolamine solution pH remains below about 10, but the zeolite structure may degrade in extended contract with aqueous alkanolamine solutions at pH levels above about 10.

Suitable zeolites include those commonly referred to as large pore, i.e., those zeolites having a Constraint Index of less than about 1, such as zeolite X, and zeolite Y as well as those commonly referred to as medium-pore, i.e., those zeolites having a Constraint Index of from about 1 to about 12. Examples of suitable medium-pore zeolites include ZSM-5, ZSM-11, ZSM-12, ZSM-22, ZSM-23, ZSM-35, and ZSM-48. Zeolite Beta, known to exhibit characteristics of either a large pore zeolite or a medium-pore zeolite, is also useful in the present invention.

The zeolite-containing catalysts useful in the present invention also include those catalysts which exhibit Constraint Indices of from about 0.1 to about 10, for example ZSM-5, MCM-22 and Zeolite Beta, although it is well recognized that the Constraint Index of zeolite Beta varies widely with temperature. Zeolite Beta is described in U.S. Pat. Nos. 4,696,732; 3,308,069, as well as Re. 28,341, the entire contents of which are incorporated by reference as if set forth at length herein.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732, cited above, discloses Constraint Index values for typical zeolite materials and is incorporated by reference as if set forth at length herein for detailed catalyst descriptions and Constraint Index values.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); U.S. Pat. No. 4,100,262 and 4,139,600, the disclosure of these is incorporated herein by reference. Zeolite ZSM-12 and the conventional preparation thereof are described in U.S. Pat. No. 3,832,449, the disclosure of which is incorporated herein by reference.

Catalysts such as ZSM-5 combined with a Group VIII metal described in U.S. Pat. No. 3,856,872, incorporated by reference as if set forth at length herein, are also useful in the present invention.

Additional catalytic materials useful in the present invention include materials which are readily identified by their characteristic X-ray diffraction patterns. In their calcined form, these synthetic porous crystalline material components which may be employed in a catalyst composition useful in the process of this invention are characterized by an X-ray diffraction pattern including the following lines:

TABLE A

| Interplanar d-Spacing (A) | Relative Intensity, $I/I_o \times 100$ |
| --- | --- |
| 12.36 ± 0.4 | M–VS |
| 11.03 ± 0.2 | M–S |
| 3.83 ± 0.14 | M–VS |
| 6.18 ± 0.12 | M–VS |
| 6.00 ± 0.10 | W–M |
| 4.06 ± 0.07 | W–S |
| 3.91 ± 0.07 | M–VS |
| 3.42 ± 0.06 | VS |

Alternatively, these materials may be characterized by an X-ray diffraction pattern in their calcined form including the following lines:

TABLE B

| Interplanar d-Spacing (A) | Relative Intensity, $I/I_o \times 100$ |
| --- | --- |
| 30.0 ± 2.2 | W–M |
| 22.1 ± 1.3 | W |
| 12.36 ± 0.4 | M–VS |
| 11.03 ± 0.2 | M–S |
| 8.83 ± 0.14 | M–VS |
| 6.18 ± 0.12 | M–VS |
| 6.00 ± 0.10 | W–M |
| 4.06 ± 0.07 | W–S |
| 3.91 ± 0.07 | M–VS |
| 3.42 ± 0.06 | VS |

More specifically, the calcined form may be characterized by an X-ray diffraction pattern including the following lines:

TABLE C

| Interplanar d-Spacing (A) | Relative Intensity, $I/I_o \times 100$ |
|---|---|
| 12.36 ± 0.4 | M–VS |
| 11.03 ± 0.2 | M–S |
| 8.83 ± 0.14 | M–VS |
| 6.86 ± 0.14 | W–M |
| 6.18 ± 0.12 | M–VS |
| 6.00 ± 0.10 | W–M |
| 5.54 ± 0.10 | W–M |
| 4.92 ± 0.09 | W |
| 4.64 ± 0.08 | W |
| 4.41 ± 0.08 | W–M |
| 4.25 ± 0.08 | W |
| 4.10 ± 0.07 | W–S |
| 4.06 ± 0.07 | W–S |
| 3.91 ± 0.07 | M–VS |
| 3.75 ± 0.06 | W–M |
| 3.56 ± 0.06 | W–M |
| 3.42 ± 0.06 | VS |
| 3.30 ± 0.05 | W–M |
| 3.20 ± 0.05 | W–M |
| 3.14 ± 0.05 | W–M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, these materials may be characterized in their calcined form by an X-ray diffraction pattern including the following lines:

TABLE D

| Interplanar d-Spacing (A) | Relative Intensity, $I/I_o \times 100$ |
|---|---|
| 30.0 ± 2.2 | W–M |
| 22.1 ± 1.3 | W |
| 12.36 ± 0.4 | M–VS |
| 11.03 ± 0.2 | M–S |
| 8.83 ± 0.14 | M–VS |
| 6.86 ± 0.14 | W–M |
| 6.18 ± 0.12 | M–VS |
| 6.00 ± 0.10 | W–M |
| 5.54 ± 0.10 | W–M |
| 4.92 ± 0.09 | W |
| 4.64 ± 0.08 | W |
| 4.41 ± 0.08 | W–M |
| 4.25 ± 0.08 | W |
| 4.10 ± 0.07 | W–S |
| 4.06 ± 0.07 | W–S |
| 3.91 ± 0.07 | M–VS |
| 3.75 ± 0.06 | W–M |
| 3.56 ± 0.06 | W–M |
| 3.42 ± 0.06 | VS |
| 3.30 ± 0.05 | W–M |
| 3.20 ± 0.05 | W–M |
| 3.14 ± 0.05 | W–M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Tables A–D, the relative intensities are given in terms of the symbols W=weak, M=medium, S=strong, VS=very strong. In terms of intensities, these may be generally designated as follows:

W=0–20
M=20–40
S=40–60
VS=60–100

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22, the synthesis and composition of which is taught in U.S. Pat. No. 4,954,325.

The zeolite hydrotreating catalyst herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be introduced in the catalyst composition by way of cocrystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing the platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the hydrotreating process of this invention, the zeolite crystals should be dehydrated, at least partially. This can be done by heating the crystals to a temperature in the range of from about 200° C. to about 595° C. in an atmosphere such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a The zeolite catalyst particles can be formed into a wide variety of shapes and sizes. Generally speaking, the particles can be in the form of a powder, a granule, a bead, or a molded product such as an extrudate, i.e., a pellet, having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the crystalline material with another material which is resistant to the temperatures and other conditions employed in the hydrotreating process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that hydrotreated products can be obtained economically and orderly without employing other means for controlling the rate of reaction. These materials may be incorporated into naturally occurring clays, e.g., bentonite and kaolin. Said materials, i.e., clays, oxides, etc., function as binders for the catalyst. These clay binders have been employed normally only for the purpose of improving the crush strength of the catalyst.

Naturally occurring clays which can be composited with zeolite crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

In addition to the foregoing materials, the crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the hydrotreating catalyst of the invention may be increased by steaming. U.S. Pat. Nos. 4,663,492; 4,594,146; 4,522,929; and 4,429,176, the entire disclosures of which are incorporated herein by reference, describe conditions for the steam stabilization of zeolite catalysts which can be utilized to steam-stabilize the catalyst for use herein. The steam stabilization conditions include contacting the catalyst with, e.g., 5–100% steam at a temperature of at least about 300° C. (e.g., 300°–650° C.) for at least one hour (e.g., 1–200 hours) at a pressure of 101–2,500 kPa. In a more particular embodiment, the catalyst can be made to undergo steaming with 75–100% steam at 315°–500° C. and atmospheric pressure for 2–25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

HYDROTREATING PROCESS

Alkanolamine degradation products are converted in the present process to products having improved acid gas sorption capacity. This conversion is referred to herein as hydrotreating because the process proceeds under hydrogen pressure over a metal-containing catalyst of the type most typically employed in the hydrotreating of petroleum fractions. But the present process employs relatively mild conditions of temperature and pressure to effect conversion of the alkanolamine by-products, as summarized below in Table 2.

TABLE 2

| | Reaction Conditions | |
|---|---|---|
| Process Variable | Broad | Preferred |
| Temperature, °C. | 30–400 | 50–300 |
| LHSV, V/V Hr. | 0.01–100 | 0.1–5 |
| Pressure, kPa | 1–14,000 | 5–700 |
| Hydrogen Dosage, Mols $H_2$/Mol alkanolamine | 0.1–100 | 1–10 |

ALKANOLAMINE REGENERATION PROCESS FLOW

Referring now to the Figure, a crude gas 10 containing $H_2S$ and $CO_2$ is charged to alkanolamine absorber column 20, where the crude gas is countercurrently contacted with lean alkanolamine solution 30 which enters alkanolamine absorber column 20 near the top. The lean alkanolamine solution absorbs the $H_2S$ and $CO_2$, purifying the gas. The purified gas stream 22 is withdrawn overhead from alkanolamine absorber column 20. Upon absorption of the $H_2S$ and $CO_2$, the lean alkanolamine solution 30 becomes a rich ethanolamine solution 34 and is withdrawn from the bottom of alkanolamine absorber column 20.

The rich alkanolamine 34 is then charged to an upper section of a stripper tower 40 and is stripped with steam 42 at about 115° C. to remove the $H_2S$ and $CO_2$ 44. Upon stripping, the rich alkanolamine 24 becomes lean alkanolamine 30. A slipstream of lean alkanolamine 46 is drawn off and filtered through a suitable medium 50 to remove particles large enough to accumulate and clog the downstream hydrotreater reactor bed and/or ion exchange resin. The filtered alkanolamine solution 52 is charged to alkanolamine hydrotreater reactor 60 where it it is held at elevated temperature of about 115° C., in the presence of a commercial hydrotreating catalyst such as Ni-Mo on an alumina binder, under relatively mild pressure of about 350 kPa at liquid hourly space velocity of about 5 $hr^{-1}$. Hydrogen pressure is maintained in the reaction zone via combined recycle and makeup hydrogen which enter the hydrotreater reactor 60 through line 72. The hydrogen makeup rate in line 74 varies according to the the impurity concentration in the alkanolamine solution, but is typically controlled to provide about 5 moles of hydrogen per mole of alkanolamine in the total hydrotreater reactor feed.

The total reaction pressure is not critical, however it is preferred to maintain hydrogen partial pressure within the hydrotreater reactor to suppress polymerization of olefinic byproducts which cloud the alkanolamine solution and typically necessitate filtration to prevent process equipment fouling.

Hydrotreated alkanolamine solution from reactor 60 flows through transfer line 64 and enters flash drum 70 to separate and recycle unreacted hydrogen from the hydrotreated liquid alkanolamine solution. Flash drum 70 may comprise any suitable vapor/liquid separation means, and is preferably equipped with a vapor disengaging pad 71 to avoid recycle of entrained liquids through the hydrogen recycle line 72.

Reactor 60 may be preceded by a pump and a process heater or heat exchanger to increase pressure and temperature as required to progress the alkanolamine hydrotreating reaction in the preferred liquid phase.

The hydrotreated alkanolamine solution may be returned to the absorber column 20 but is preferably processed further to remove heat stable inorganic salts, for example, as taught in U.S. Pat. No. 4,795,565 to Yan. Thus, in a preferred embodiment, the hydrotreated alkanolamine liquid 76 from flash drum 70 flows to one or more ion-exchange zones, schematically represented in the Figure as a single ion-exchange vessel 80. The ion-exchange stage preferably includes contacting the alkanolamine solution with anionic and cationic exchange resins in series. The weak anionic and cationic exchange resins are particularly preferred. The regenerated alkanolamine solution is then returned to the alkanolamine absorber via lines 84 and 30 to be continuously recirculated through acid gas sorption and desorption stages as described above.

EXAMPLE

An aqueous, diethanolamine (DEA) solution containing about 20% by weight DEA, 30% by weight other organics including DEA degradation products, and about 0.1% by weight total residual $H_2S+CO_2$ is charged at a rate of 50 cc/hr to a stainless steel reactor containing approximately 50 cc of a commercial hydrotreating catalyst. The column is heated with annular electric resistance heaters to maintain the hydrotreating reaction temperature at about 240° C. The system is maintained under pressure pressure of about 350 kPa with a hydrogen gas cofeed of about 5 mols $H_2$/mol alkanolamine. The following analysis of the products is shown in Table 3, below. Comparison of the feed and product compositions reveals a net loss of NTO and BHEP (structures shown above in Table 1) coupled with a net gain of 11.5 grams of DEA, per 100 grams of aqueous DEA solution feed indicating conversion of degradation products to DEA. The acid absorption capacity index (AACI), defined as the sum of the weight percent DEA and one-half (½) the weight percent BHEP, increases 35%, from 25.87 to 34.87 upon hydrotreating in accordance with the present process.

TABLE 3

|  | Feed, g. | Product, g |
| --- | --- | --- |
| DEA | 20.36 | 31.86 |
| BHEP | 11.14 | 6.01 |
| NTO | 20.56 | 16.73 |
| $H_2O$ | 48.00 | 46.00 |
| AACI | 25.87 | 34.87 |
| Relative AACL | 1.00 | 1.35 |

Changes and modifications in the specifically described embodiments can be carried out without departing from the scope of the invention which is intended to be limited only by the scope of the appended claims.

What is claimed is:

1. A method for increasing the AACI of an aqueous diethanolamine solution which has been at least partially deactivated from contact with an acid gas, said method comprising contacting said aqueous diethanolamine solution with hydrogen in the presence of a hydrotreating catalyst under conversion conditions of temperature from 30° C. to 400° C., liquid hourly space velocity from 0.01 $hr^{-1}$ to 100 $hr^{-1}$, pressure from 1 to 14,000 kPa, hydrogen dosage from 1 to 100 mols $H_2$ per mol of diethanolamine, and contact time sufficient to convert diethanolamine degradation products to diethanolamine.

2. The process of claim 1 further comprising filtering said aqueous diethanolamine solution to remove particulates before contacting said aqueous diethanolamine solution with hydrogen.

3. The process of claim 1 further comprising:
   (a) contacting said aqueous diethanolamine solution with an anionic exchange resin; and
   (b) contacting said aqueous diethanolamine solution with a cationic exchange resin.

4. The process of claim 1 wherein said catalyst comprises at least one hydrogenation component selected from a metal, a metal sulfide, and a metal oxide, said hydrogenation component deposited on a support.

5. The process of claim 4 wherein said hydrogenation component further comprises at least one selected from the group consisting of Group IB, VIB and Group VIIIA metals.

6. The process of claim 4 wherein said support comprises at least one selected from the group consisting of silica, alumina, silica-alumina, titania, magnesia, clays, zeolites, and active carbon.

7. The process of claim 1 wherein said catalyst comprises a zeolite having a Constraint Index of less than about 12.

8. The process of claim 7 wherein said catalyst comprises a zeolite having a Constraint Index of from about 1 to about 12.

9. The process of claim 1 wherein said catalyst comprises a synthetic crystalline material characterized by the X-ray diffraction pattern including the interplanar d-spacings as set forth in Table A of the specification.

10. The process of claim 1 wherein said catalyst comprises a synthetic crystalline material characterized by the X-ray diffraction pattern including the interplanar d-spacings as set forth in Table B of the specification.

11. The process of claim 1 wherein said catalyst comprises a synthetic crystalline material characterized by the X-ray diffraction pattern including the interplanar d-spacings as set forth in Table C of the specification.

12. The process of claim 1 wherein said catalyst comprises a synthetic crystalline material characterized by the X-ray diffraction pattern including the interplanar d-spacings as set forth in Table D of the specification.

13. The process of claim 1 wherein said hydrotreating conversion conditions are temperature of from 50° C. to 300° C., liquid hourly space velocity of from 0.1 $hr^{-1}$ to 5 $hr^{-1}$, pressure of from 5 to 700 kPa, and hydrogen dosage of from 1 to 10 mols $H_2$ per mol of diethanolamine.

14. A method for increasing the AACI of an aqueous diethanolamine solution being at least partially deactivated from contact with an acid gas, said regeneration method comprising:
   (a) filtering said aqueous diethanolamine solution to remove suspended particulates;
   (b) contacting said filtered aqueous diethanolamine solution with an anionic ion-exchange resin;
   (c) contacting said aqueous diethanolamine solution with a cationic exchange resin;
   (d) reacting said aqueous diethanolamine solution with hydrogen in the presence of a hydrotreating catalyst under hydrotreating conversion conditions of temperature from 30° C. to 400° C., liquid hourly space velocity of from 0.1 hr$^{-1}$ to 100 hr$^{-1}$, pressure of from 1 to 14,000 kPa, hydrogen dosage from 1 to 100 mols H$_2$ per mol of diethanolamine, and contact time sufficient to evolve a product stream having a higher concentration of diethanolamine that said at least partially deactivated diethanolamine solution.

15. The process of claim 14 wherein said catalyst comprises at least one hydrogenation component selected from a metal, a metal sulfide, and a metal oxide, said hydrogenation component deposited on a support.

16. A process for removing at least one of H$_2$S, CO$_2$ and CO from a hydrocarbon gas stream containing the same comprising the steps of:

(a) providing a hydrocarbon gas stream containing a recoverable concentration of H$_2$S, CO$_2$ or CO;

(b) contacting said hydrocarbon gas stream of step (a) with an aqueous alkanolamine solution containing alkanolamine to remove H$_2$S, CO$_2$ or CO from said hydrocarbon gas stream, to convert at least a portion of said alkanolamine to degradation products having a lesser affinity for sorbing acid gases than said alkanolamine, and to evolve an alkanolamine solution enriched in H$_2$S, CO$_2$ or CO;

(c) stripping H$_2$S, CO$_2$ or CO from said enriched alkanolamine solution of step (b) to evolve a lean alkanolamine solution containing both alkanolamine and said alkanolamine degradation products;

(d) heating at least a portion of said lean aqueous alkanolamine stream of step (c) to elevated temperature and holding said lean aqueous alkanolamine solution of step (c) at said elevated temperature under hydrogen pressure in the presence of a hydrotreating catalyst for a period of time sufficient to rejuvenate said lean alkanolamine solution such that the rejuvenated lean alkanolamine solution exhibits increased acid gas sorption capacity per unit mass than stripped lean alkanolamine solution of step (c).

17. The process of claim 16 wherein said hydrotreating catalyst comprises at least one hydrogenation component selected from a metal, a metal sulfide, and a metal oxide, said hydrogenation component deposited on a support.

18. The process of claim 17 wherein said hydrogenation component further comprises at least one selected from the group consisting of Group IB, VIB and Group VIIIA metals.

19. The process of claim 17 wherein said support comprises at least one selected form the group consisting of silica, alumina, silica-alumina, titania, magnesia, clays, zeolites, and active carbon.

20. A method for increasing the acid gas sorption capacity of an aqueous alkanolamine solution which has been at least partially deactivated from contact with an acid gas, said method comprising contacting said aqueous alkanolamine solution with hydrogen in the presence of a hydrotreating catalyst under conversion conditions of temperature from 30° C. to 400° C., liquid hourly space velocity from 0.01 hr$^{-1}$ to 100 hr$^{-1}$, pressure from 1 to 14,000 kPa, hydrogen dosage from 1 to 100 mols H$_2$ per mol of alkanolamine, and contact time sufficient to convert alkanolamine degradation products to alkanolamine.

21. The method of claim 20 further comprising filtering said aqueous alkanolamine solution to remove particulates before contacting said aqueous alkanolamine solution with hydrogen.

22. The method of claim 20 further comprising:

(a) contacting said aqueous alkanolamine solution with an anionic exchange resin; and (b) contacting said aqueous alkanolamine solution with a cationic exchange resin.

23. The method of claim 20 wherein said catalyst comprises at least one hydrogenation component selected from a metal, a metal sulfide, and a metal oxide, said hydrogenation component deposited on an a support.

24. The method of claim 23 wherein said hydrogenation component further comprises at least one selected from the group consisting of Group IB, VIB, and Group VIIIA metals.

25. The method of claim 23 wherein said hydrogenation component further comprises at least one selected from the group consisting of silica, alumina, silica-alumina, titania, magnesia, clays, zeolites, and active carbon.

26. The method of claim 20 wherein said catalyst comprises a zeolite having a Constraint Index of less than about 12.

27. The method of claim 20 wherein said catalyst comprises a synthetic crystalline material characterized by the X-ray diffraction pattern including the interplanar d-spacings as set forth in Table A of the specification.

28. The method of claim 20 wherein said catalyst comprises a synthetic crystalline material characterized by the X-ray diffraction pattern including the interplanar d-spacings as set forth in Table B of the specification.

29. The method of claim 20 wherein said catalyst comprises a synthetic crystalline material characterized by the X-ray diffraction pattern including the interplanar d-spacings as set forth in Table C of the specification.

30. The method of claim 20 wherein said catalyst comprises a synthetic crystalline material characterized by the X-ray diffraction pattern including the interplanar d-spacings as set forth in Table D of the specification.

* * * * *